US005591225A

United States Patent [19]
Okuda

[11] Patent Number: 5,591,225
[45] Date of Patent: Jan. 7, 1997

[54] COMPOSITE ARTIFICIAL BLOOD VESSEL

[75] Inventor: Yasuhiro Okuda, Osaka, Japan

[73] Assignee: Vascular Craft Research Center Co., Ltd., Tokyo, Japan

[21] Appl. No.: 347,156

[22] Filed: Nov. 23, 1994

Related U.S. Application Data

[63] Continuation of Ser. No. 952,734, filed as PCT/JP92/00373, Mar. 27,1992 published as WO92/17218, Oct. 15, 1992, abandoned.

[30] Foreign Application Priority Data

Mar. 29, 1991 [JP] Japan .................................. 3-066070

[51] Int. Cl.$^6$ .................................. A61F 2/06; A61F 2/04
[52] U.S. Cl. .................................. 623/1; 623/12
[58] Field of Search .................................. 623/1, 11, 12; 600/36

[56] References Cited

U.S. PATENT DOCUMENTS

| | | | |
|---|---|---|---|
| 4,208,745 | 6/1980 | Okita | 623/1 |
| 5,028,597 | 7/1991 | Kodama et al. | 623/11 |
| 5,118,524 | 6/1992 | Thompson et al. | 623/1 |

FOREIGN PATENT DOCUMENTS

| | | |
|---|---|---|
| 3918889 | 2/1990 | Australia . |
| 3988289 | 3/1990 | Australia . |
| 0246638 | 11/1987 | European Pat. Off. . |
| 0415845 | 8/1990 | European Pat. Off. . |
| 8401892 | 5/1984 | WIPO . |
| 9005755 | 5/1990 | WIPO . |

OTHER PUBLICATIONS

C. A. Costello et al, "Surface–Selective Introduction of Specific Functionalities onto Poly(tetrafluoroethylene)[1]" Macromolecules, 1987, 20, 2819–2828.

Hegazy et al, "Radiation–Initiated Graft Copolymerization of Individual Monomer and Comonomer onto Polyethylene and Polytetrafluoroethylene Films", J. Appl. Polym. Sci., 39, 1029–1043 (1990).

Chapiro et al, "Synthesis of Permselective Membranes by Radiation Induced Grafting of Hydrophilic Monomers into Poly(Tetrafluoroethylene) Films", Polymer Engineering And Science, Feb. 1980, 20 (3), 202–205.

Morel et al, "Structure and Morphology of Poly(Tetrafluoroethylene)–Poly(N–Vinylpyrrolidone) Copolymer Membranes" Journal of Applied Polymer Science, vol. 24, 771–780, (1979).

Aiba et al, "Preparation of Poly(Styrenesulfonic Acid)–Grafted Microporous Polytetrafluoroethylene Membranes and Their Activity as Hydrolysis Catalysts", Makromol. Chem., Rapid Commun., 7, 91–96 (1986).

Tanfani et al, "Glycidyl Acrylate Plasma Glow Discharged Polymers", Biomaterials, 1990, vol. 11, Oct. 585–589.

Massia et al, "Human Endothelial Cell Interactions With Surface–Coupled Adhesion Peptides on a Nonadhesive Glass Substrate and Two Polymeric Biomaterials", J. Biomedical Materials Research, vol. 25, 223–242 (1991).

(List continued on next page.)

*Primary Examiner*—Debra S. Brittingham
*Attorney, Agent, or Firm*—Cushman Darby & Cushman Intellectual Property Group of Pillsbury Madison & Sutro LLP

[57] ABSTRACT

An artificial blood vessel comprising a tube of a porous synthetic polymer on a surface of which a protein or a peptide having cell adhesion and growth functions is covalently bonded through hydroxyl groups, carboxyl groups, epoxy groups or amino groups. Its surface is uniformly composited stably with the material having the tissue induction function by the covalent bond without deforming a shape of the porous synthetic polymer material. Therefore, no initial thrombus is induced, and the intima is quickly formed and remains stably for a long time.

5 Claims, 2 Drawing Sheets

OTHER PUBLICATIONS

Okada et al, "Evaluation of Collagen–Immobilized Percutaneous Implants", Polym. Mater. Sci. Eng., 548–552 (1988).

Dekker et al, "Adhesion of Endothelial Cells and Adsorption of Serum Proteins on Gas Plasma–Treated Polytetrafluoroethylene", Biomaterials, 1991, vol. 12, 130–138.

Ramalanjaona et al, "The Effect of Fibronectin Coating on Endothelial Cell Kinetics in Polytetrafluoroethylene Grafts", J. Vascular Surgery, 3(2), 264–272, (1986).

Seeger et al, "Improved in Vivo Endothelialization of Prosthetic Grafts by Surface Modification With Fibronectin" J. Vascular Surgery, 8 (4), 476–482 (1988).

Schneider et al, "Preformed Confluent Endothelial Cell Monolayers Prevent Early Platelet Deposition on Vascular Prostheses in Baboons", J. Vascular Surgery, 8 (3), 229–235 (1988).

Kesler et al, "Enhanced Strength of Endothelial Attachment on Polyester Elastomer and Polytetrafluoroethylene Graft Surfaces With Fibronectin Substrate", J. Vascular Surgery, 3(1), 58–64 (1986).

Scott et al, "A Collagen Coated Vascular Prosthesis", J. Cardiovasc. Surg., 28, 498–504 (1987).

COMPOSITE ARTIFICIAL BLOOD VESSEL

This is a continuation of application Ser. No. 07/952,734, filed as PCT/JP92/00373, Mar. 27, 1992 published as WO92/17218, Oct. 15, 1992, now abandoned.

FIELD OF THE INVENTION

The present invention relates to an artificial blood vessel used for treatment of diseases in aortas, coronary arteries, peripheral blood vessels and the like.

PRIOR ART

Hitherto, a tube of a woven or knitted fabric of polyester fibers or expanded polytetrafluoroethylene (hereinafter referred to as "EPTFE") is used as an artificial blood vessel. The EPTFE tube is practically used in a smaller diameter range than the polyester tube, since polytetrafluoroethylene itself is excellent in an anti-thrombotic property and a porous structure comprising fibers and nodes which is obtained by drawing is excellent in biocompatibility.

However, EPTFE is not necessarily satisfactory in the anti-thrombotic property. In the case of an artificial blood vessel having an inner diameter of 6 mm or less, in particular 4 mm or less, a sufficient patency ratio is not achieved. To solve this problem, the following methods have been studied: (1) improvement of an anti-thrombotic property of a material itself, (2) imparting an anti-thrombotic property to an artificial blood vessel by forming an intima through induction of a tissue in an early stage after grafting the artificial blood vessel and (3) seeding vascular endothelial cells having a good anti-thrombotic property on an inner wall of the artificial vessel.

Concretely, as the method (1), a development of an anti-thrombotc polymer material having a microphase separation structure or an anti-thrombotic agent-immobilized material is discussed (cf. Noishiki et al, Trans. A. S. A. I. O., 23, 253 (1977), etc.) Though such anti-thrombogenic materials can prevent the formation of thrombuses immediately after grafting, after a long term from the grafting, the thrombi are formed so that the vessel is occuluded.

As the method (2), is proposed an artificial blood vessel on which a cell-adhering protein such as collagen and fibronectin is coated and immobilized by crosslinking (cf. C. H. Lundgren et al, Trans. A. S. A. I. O., 32 346 (1986), etc.). Since the thrombus tends to adhere due to the coating of the protein in such artificial blood vessel, the patency ratio greatly decreases. Then, an artificial blood vessel to which an anti-thrombotic agent such as heparin is further composited is proposed, but sufficient patency is not achieved. If the patency is maintained, the artificial blood vessel does not have sufficient properties after a long time, since the patency ratio decreases due to thickening or peeling-off of the formed intima.

As the method (3), a method for seeding the vascular endothelial cells on the inner wall of the artificial vessel is studied (cf. Takagi et al, JINKOZOKI (Japanese Journal of Artificial Organs), 17, 679 (1988), Japanese Patent Kokai Publication No. 170466/1989, etc.) However, it lacks immediate use since it takes a long time for collecting and culturing the vascular endothelial cells. In addition, stability and functions of the seeded endothelium are not complete and no good patency ratio is achieved.

As explained above, the prior arts cannot provide an artificial blood vessel which maintains a good patency ratio for a long time from the initial stage of the grafting.

SUMMARY OF THE INVENTION

As a result of the study on an artificial blood vessel in which an intima can be formed thereon quickly after grafting, the formed intima will be present stably and have a good patency ratio for a long time and an initial patency is good, it has been found that an artificial blood vessel, to which a protein or a peptide having cell adhesion and growth functions is covalently bonded through hydroxyl groups, carboxyl groups, epoxy groups or amino groups which are introduced on a surface of a porous synthetic polymer material by a physical or chemical treatment, is excellent in initial patency after grafting, an intima is quickly formed thereon, and the formed intima will be present stably for a long time without thickening or peeling-off of the formed intima so that a good patency ratio continues. Thereby, the present invention has been completed.

Accordingly, the present invention provides an artificial blood vessel comprising a tube of a porous synthetic polymer on a surface of which a protein or a peptide having cell adhesion and growth functions is covalently bonded through hydroxyl groups, carboxyl groups, epoxy groups or amino groups.

DETAILED DESCRIPTION OF THE INVENTION

Figure 1:
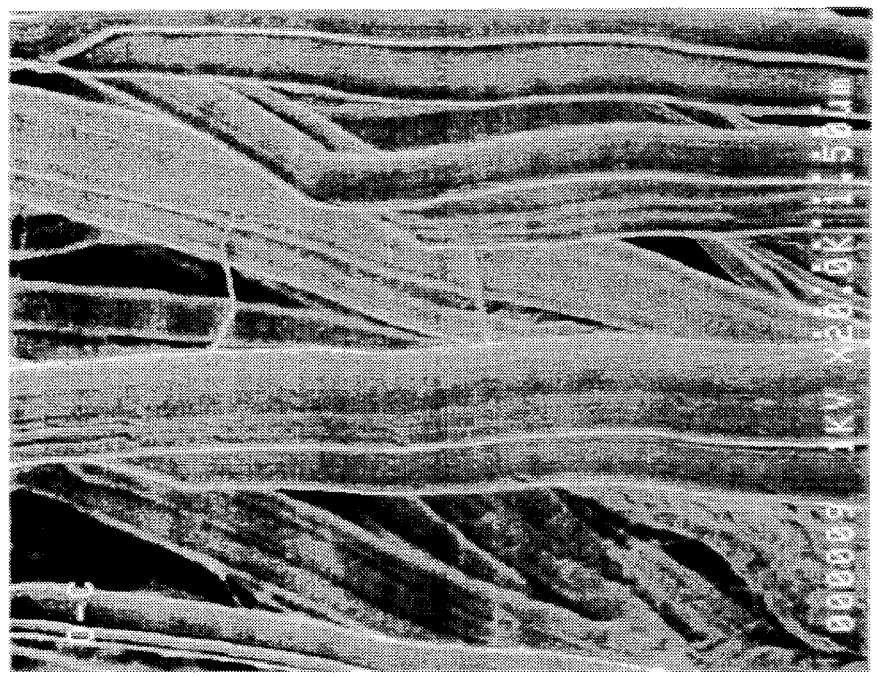
FIG. 1 is a scanning electron microphotograph of an inner surface of the artificial blood vessel of Example 1 comprising EPTFE to which gelatinated atelocollagen is chemically bonded.

As the porous synthetic polymer material used in the artificial blood vessel of the present invention, a polyester woven or knitted fabric tube and a EPTFE tube which give satisfactory results are preferred since they have sufficient strength as the artificial blood vessel, are not decomposed or deteriorated in an organism and have no toxicity. Among them, the EPTFE tube is particularly preferred, which has a microporous structure comprising fibers and nodes, a high porosity and good compatibility with the tissue.

To form the intima in an early stage and maintain the formed intima stably, it is necessary to introduce the tissue or blood capillaries in the porous material. To this end, the porosity of the porous synthetic polymer material is at least 50% preferably at least 70%.

For the same reason, a pore diameter is preferably at least 20 μm. In particular, in the case of EPTFE, the pore diameter is preferably from 20 to 200 μm.

A ratio of an area of the synthetic polymer material which occupies the inner surface contacting a blood stream in the artificial blood vessel is from 15 to 80%, preferably from 25 to 55%. This area ratio can be determined using a scanning electron microscope. When the area ratio of the synthetic polymer material is too high, a contact area between the immobilized protein or peptide and the blood is too large and a possibility of the thrombus formation becomes high so that the initial patency ratio decreases. When the area ratio of the synthetic polymer material is too low, the acceleration effect of the immobilized protein or peptide on the formation of the intima is not sufficiently achieved.

To introduce the functional groups on the surface of the synthetic polymer material, there may be used a chemical treatment, or a physical treatment such as radiation exposure with a γ-ray or an electron beam and treatment with corona discharge or glow discharge. A suitable method is selected according to the polymer material. For example, in the case of polyethylene terephthalate (PET) which is one of the polyesters, ester linkages are hydrolyzed with an acid or an alkali to form the carboxyl groups, which are then converted to the ester groups, the hydroxyl groups, the amino groups or the epoxy groups by known reactions. It is possible to carry out graft polymerization by the irradiation of UV light or the corona discharging.

In the case of EPTFE, after defluorination with an alkali metal compound, the carboxyl groups, the hydroxyl groups, the amino groups, the epoxy or the like are introduced in EPTFE by reacting a compound having such functional groups.

Examples of the alkali metal compound are methyl-lithium, n-butyllithium, tert.-butyllithium, sodium-naphthalenide, naphthalene-benzophenone, vinyllithium and the like. They are used in the form of a solution. Among them, sodium-naphthalenide and sodium-benzophenone will form a dark brown layer on the EPTFE surface after treatment, and cannot treat EPTFE to the porous inner part uniformly. So, methyllithium, n-butyllithium and tert.-butyllithium are preferred to produce the artificial blood vessel of the present invention. Since each of methyllithium, n-butyllithium and tert.-butyllithium has a weak force to withdraw the fluorine atom, it is necessary to add a chelating agent such as hexamethylphosphoric triamide or N,N,N,N-tetramethylethylenediamine.

Examples of the compound having the hydroxyl group, the carboxyl group, the epoxy group or the amino group are glycerol (meth)acrylate, 2-hydroxyethyl (meth)acrylate, 2-hydroxypropyl (meth)acrylate, polyethyleneglycol (meth)acrylate, glycidyl (meth)acrylate, (meth)acrylic acid, allylamine, 2-aminoethyl (meth)acrylate, acrylamide and the like. Alternatively, an acid anhydride such as maleic anhydride is added and then hydrolyzed.

More specifically, for example, the EPTFE tube is dipped in a solution of methyllithium in diethyl ether in a nitrogen atmosphere and hexamethylphosphoric triamide is added to the solution. Then, the solution containing the tube is kept standing for 30 minutes at 0° C. to withdraw the fluorine atoms from EPTFE. After removing the solution, a solution of acrylic acid in tetrahydrofuran is added and reacted at 60° C. for 10 hours. After the reaction, excessive acrylic acid or its polymer is washed off to obtain the acrylic acid-grafted polymer.

To introduce the functional groups in EPTFE, radiation exposure with the γ-ray or the electron beam, or the corona discharge may be used. But, as is well known, by the radiation exposure treatment, EPTFE is decomposed to its deep crystalline part so that a molecular weight of PTFE is lowered and its strength is considerably decreased and such EPTFE tube can hardly be used as the artificial blood vessel practically (cf. G. Morel et al, J. Appl. Polym. Sci., 24, 771 (1979)). With the glow discharge, it is difficult to treat the deep porous part of EPTFE so that only the outer and inner surfaces of the tube can be treated. Thereby, it is difficult to immobilize the protein on the pore surfaces in tube wall, and the formation of the tissue in the wall or the introduction of the blood capillaries cannot be accelerated.

On the other hand, treatment with the alkali metal compound can make the EPTFE tube to its porous inner part uniformly and also to the deep crystalline part of EPTFE without decomposing PTFE with a depth of about several hundred angstroms from the surface. Therefore, the strength is not decreased and the protein or peptide can be immobilized in all the parts of the porous wall. Consequently, it is desirable to treat the porous polymer material with the alkali metal compound for the production of the composite artificial blood vessel of the present invention.

A method for immobilizing the protein or peptide may be selected according to the material. Preferably, the method is selected so that the tissue induction function is not lost by the immobilization and the protein or peptide is immobilized by a bond which will remain without cleavage till the intima is formed. For example, with the hydroxyl group, the carboxyl group or the amino group, the covalent bond is formed by dehydration condensation, and with the epoxy group, the covalent bond is formed by an addition reaction. With the hydroxyl group, the protein or peptide is directly bonded by the dehydration condensation in the presence of carbodiimide as a catalyst, or an eliminating group such as a trifluoromethanesulfonyl group is introduced to improve the reactivity and then such group is reacted with the amino group of the protein. With the carboxyl group, the protein or peptide is directly bonded using a dehydration condensation catalyst such as carbodiimide, or N-hydroxysuccinimide is reacted to introduce an active ester group and improve the reactivity and then the active ester group is reacted with an amino acid of the protein.

The surface which is treated by coating and crosslinking in the prior arts has unevenness of several μm or larger and it is difficult to cover the entire surface of the porous synthetic polymer material. When the protein or peptide is immobilized according to the present invention, the surface unevenness is less than 50 nm and the pore cavities are completely covered.

As the protein to be composited, cell adhesion proteins, endothelial cell growth factors, blood vessel growth factors and the like are exemplified. Among them, collagen, gelatin, albumin, laminin and fibronectin are preferred.

Since the protein or peptide is not covalently bonded to the porous polymer in the conventional coating-crosslinking type composite artificial blood vessel, there are many drawbacks that the coated protein or peptide is easily peeled off, uniformity in the pores is not sufficient, some parts may not be covered or some parts are coated too thick, or aggregates of the protein are deposited. Thereby, the initial patency ratio is low, the formed intima has poor stability and no good patency ratio is maintained for a long time.

The composite artificial blood vessel of the present invention comprises a porous synthetic polymer material, in particular EPTFE on which surface the protein or peptide having the cell adhesion and cell propagation functions is chemically bonded, and such protein or peptide strongly covers the whole surface of the porous wall of the polymer material covalently at a thickness in a submicron order. The surface unevenness of the composite material is less than 50 nm, and it is possible to impart the tissue induction function to the surface without materially changing the shape of the porous synthetic polymer material. Since the surface of the porous polymer material is thinly composited, its shape is not changed by compositing. Therefore, an area on which the protein or peptide is immobilized or an amount of the protein or peptide can be controlled by the porous structure of the synthetic polymer material.

As explained above, since the protein or peptide is strongly immobilized on the polymer material by the covalent bond, it is not peeled off during the handling in operation. Since the surface unevenness is less than 50 nm, the unevenness formed by the compositing does not induce the formation of thrombus by the blood rheology so that the patency ratio does not decrease after the grafting. Since, in the composite artificial blood vessel of the present invention, the tissue induction material is thinly composited only on the surface of the porous synthetic polymer material, no protein or peptide is present in the voids of the porous material. Therefore, the coated area and the composited amount of the protein or peptide can be controlled by changing the porous structure of the synthetic polymer material. As the result, since the contact area of the protein and the blood can be changed, the composite structure is controlled with balancing the thrombus formation due to compositing and the acceleration effect on the formation of the intima.

In the composite artificial blood vessel of the present invention, since the whole surface of the porous wall is composited with the tissue induction material, the tissue component is quickly introduced from outside the of the artificial blood vessel wall and the growth of the intima quickly proceeds from an anastomotic site. In addition, since protein or peptide is strongly and uniformly immobilized by the covalent bond, the formed intima will not be peeled off and will be present stably for a long time.

PREFERRED EMBODIMENTS OF THE INVENTION

EXAMPLE 2

In a mixture of a solution of methyllithium in ether (1.4M) (20 ml) and hexamethylphosphoric triamide (2 ml), an EPTFE tube having an average fibril length of 30 μm, a porosity of 72%, an area of the inner surface occupied by the resin of 45%, an inner diameter of 1.5 mm, an outer diameter of 2.5 mm and a length of 10 mm was dipped at 0° C. for 30 minutes in a nitrogen atmosphere, and the solution mixture was removed. Then, a solution of acrylic acid (1 g) in tetrahydrofuran (20 ml) was added and reacted at 60° C. for 10 hours.

Thereafter, unreacted acrylic acid and polymerized acrylic acid were washed off to obtain an acrylic acid-grafted EPTFE tube. A grafted amount of acrylic acid was 45 μg per 1 cm of the tube.

An aqueous solution of 0.3% gelatinated atelocollagen (hereinafter referred to as "GAC") which was prepared by thermally denaturing 0.3% solubilized atelocollagen (Nitta Gelation Cellmatrix I-P) and 0.3% 1-ethyl-3-(3-dimethylaminopropyl)carbodiimde was treated with 1N hydrochloric acid to adjust pH at 1.5. To this solution, the above prepared acrylic acid-grafted EPTFE tube was dipped for 24 hours and washed with water to obtain the GAC-bonded EPTFE tube.

The bonded amount of GAC was measured by the ninhydrin method to find that 55 μg of GAC was bonded per 1 cm of the tube.

The inner surface of the tube was observed by a scanning electron microscope. The microstructure of the fibrils and nodes of EPTFE was completely maintained, and the unevenness of the composited surface was less than 10 nm. No large unevenness which is seen in the coating complexing method was observed. The composited GAC was not peeled off by the handling such as flexing.

This artificial blood vessel had a tensile strength of 3.2 kg and a suture strength of 142 g, which were not significantly decreased from the values of 3.3 kg and 150 g of the untreated EPTFE, and the strength of this artificial blood vessel was practically acceptable. The suture strength is a load with which the tube is torn when a wire having a diameter of 0.2 mm is threaded at a position 3 cm apart from the tube end and pulled.

Each of six treated tubes was inplanted in an abdominal aorta of a rat. After three weeks, the inside of the porous wall of the artificial blood vessel was filled with the tissue components such as fibroblasts. A rate of the endothelical cell-covered area of the inner wall was 100% and a patency ratio was 100%. The patency ratio did not decrease even after one year, the 100% patency ratio was maintained, the formed intima was stable and no deposition such as thrombus was observed.

EXAMPLE 2

In a mixture of a solution of methyllithium in ether (1.4M) (20 ml) and hexamethylphosphoric triamide (2 ml), an EPTFE tube having an average fibril length of 30 μm, a porosity of 72%, an area of the inner surface occupied by the resin of 45%, an inner diameter of 2.0 mm, an outer diameter of 3.0 mm and a length of 20 mm was dipped at 0° C. for 30 minutes in a nitrogen atmosphere, and the solution mixture was removed. Then, a solution of acrylic acid (1 g) in tetrahydrofuran (20 ml) was added and reacted at 60° C. for 10 hours.

Thereafter, unreacted acrylic acid and polymerized acrylic acid were washed off to obtain an acrylic acid-grafted EPTFE tube. A grafted amount of acrylic acid was 45 μg per 1 cm of the tube.

An aqueous solution of 0.3% gelatinated atelocollagen (GAC) which was prepared by thermally denaturing 0.3% solubilized atelocollagen (Nitta Gelation Cellmatrix I-P) and 0.3% 1-ethyl-3-(3-dimethylaminopropyl)carbodiimde was treated with 1N hydrochloric acid to adjust pH at 1.5. To this solution, the above prepared acrylic acid-grafted EPTFE tube was dipped for 24 hours and washed with water to obtain the GAC-bonded EPTFE tube.

The bonded amount of GAC was measured by the ninhydrin method to find that 55 μg of GAC was bonded per 1 cm of the tube.

The inner surface of the tube was observed by a scanning electron microscope. The microstructure of the fibers and nodes of EPTFE was completely maintained, and the unevenness of the composited surface was less than 10 nm. A large unevenness which is seen in the coating complexing method was not observed. The composited GAC was not peeled off by the handling such as flexing.

Each of six treated tubes was inplanted in a carotid artery of a rabbit. After four weeks, the inside of the porous wall of the artificial blood vessel was filled with the tissue components such as fibroblasts. A rate of the endothelial cell-covered area of the inner wall was 95% and a patency ratio was 100%. The patency ratio did not decrease even after one year, the 100% patency ratio was maintained, the formed intima was stable and no deposition such as thrombus was observed.

EXAMPLE 3

In the same manner as in Example 2, 2-hydroxyethyl acrylate was grafted on the same EPTFE tube as used in Example 2. The grafted amount was 65 µg per 1 cm of the tube.

This tube was dipped in a solution of 2,2,2-trifluoroethanesulfonic acid (1 ml) and triethylamine (1 ml) in diethyl ether (20 ml) and reacted for 4 hours to introduce the 2,2,2-trifluoroethanesulfonic acid groups on the hydroxyl groups.

Then, fibronectin (derived from bovine plasma, manufactured by Nippon Ham) (5 mg) was dissolved in a sodium carbonate buffer (pH=7) (20 ml). In this solution, the above prepared tube was dipped for 24 hours and washed with water to obtain the fibronectin-bonded EPTFE tube.

The bonded amount of fibronectin was measured by the ninhydrin method to find that 40 µg of fibronectin was bonded per 1 cm of the tube.

The inner surface of the tube was observed by a scanning electron microscope. The microstructure of the fibers and nodes of EPTFE was completely maintained, and the unevenness of the composited surface was less than 10 nm. A large unevenness which is seen in the coating complexing method was not observed. The composited fibronectin was not peeled off by the handling such as flexing.

Each of six treated tubes was inplanted in a carotid artery of a rabbit. After four weeks, the inside of the porous wall of the artificial blood vessel was filled with the tissue components such as fibroblasts. A rate of the endothelial cell-covered area of the inner wall was 85% and a patency ratio was 83% (5/6). The patency ratio did not decrease even after one year, the 83% patency ratio was maintained, the formed intima was stable and no deposition such as thrombus was observed.

EXAMPLE 4

A polyester knit tube having an average pore size of 60 µm, a porosity of 60%, an area of the inner surface occupied by the resin of 50%, an inner diameter of 2.0 mm, an outer diameter of 3.0 mm and a length of 20 mm was subjected to hydrolysis with 6N hydrochloric acid to form carboxyl groups.

An aqueous solution of 0.3% gelatinated atelocollagen (GAC) which was prepared by thermally denaturing 0.3% solubilized atelocollagen (Nitta Gelation Cellmatrix I-P) and 0.3% 1-ethyl-3-(3-dimethylaminopropyl)carbodiimde was treated with 1N hydrochloric acid to adjust pH at 1.5. To this solution, the above prepared tube was dipped for 24 hours and washed with water to obtain the GAC-bonded EPTFE tube.

The bonded amount of GAC was measured by the ninhydrin method to find that 25 µg of GAC was bonded per 1 cm of the tube.

The inner surface of the tube was observed by a scanning electron microscope. The shape of the polyester fibers was completely maintained, and the unevenness of the composited surface was less than 10 nm. A large unevenness which is seen in the coating complexing method was not observed. The composited GAC was not peeled off by the handling such as flexing.

Each of six treated tubes was inplanted in a carotid artery of a rabbit. After four weeks, the inside of the porous wall of the artificial blood vessel was filled with the tissue components such as fibroblasts. A rate of the endothelial cell-covered area of the inner wall was 95% and a patency ratio was 83% (5/6). The patency ratio did not decrease even after one year, the 83% patency ratio was maintained, the intima was stable and no deposition such as thrombus was observed.

Comparative Example 1

Each of the six EPTFE tubes which were the same as that used in Example 1 was inplanted in a abdominal aorta of a rat. After three weeks, a patency ratio was 100%. But, the tissue components such as fibroblast was hardly introduced inside the porous wall of the artificial blood vessel, and a rate of the endothelial cell-covered area of the inner wall was 50%. After one year, the patency ratio decreased to 67%, and with the tubes having the patency, partial stenosis was observed.

Comparative Example 2

In the inside of the the same EPTFE tube as used in Example 1, the same 0.3% GAC solution as that used in Example 1 was injected in vacuo and crosslinked with glutaraldehyde, followed by drying. A composited amount of GAC was 0.2 mg/cm.

The inner surface of the tube was observed by a scanning electron microscope. The composited GAC formed films between the fibrils of EPTFE partially, and unevenness of 0.5 to 1 µm was formed on the surface. Some parts of the inner wall were not covered by GAC. When this composite artificial blood vessel was flexed at a radius of curvature of 5 mm repeatedly, GAC was easily peeled off.

Each of six treated tubes was inplanted in an abdominal aorta of a rat. After three weeks, a patency ratio decreased to 67%, and the endothelial cell-covered area of the inner wall was 85% in the tubes having the patency. After one year, the patency ratio was further decreased to 33%, and with the tubes having the patency, the formed intima were peeled off and partial stenosis was observed.

Comparative Example 3

Each of the six EPTFE tubes which were the same as that used in Example 2 was inplanted in a carotid artery of a rabbit. After four weeks, a patency ratio was 100%. However, substantially no tissue component such as fibroblast was introduced inside the porous wall of the artificial blood vessel, and a rate of the endothelial cell-covered area of the inner wall was 50%. After one year, the patency ratio decreased to 33%, and with the tubes having the patency, partial stenosis was observed.

Comparative Example 4

In the inside of the the same EPTFE tube as used in Example 2, the same 0.3% GAC solution as that used in Example 1 was injected in vacuo and crosslinked with glutaraldehyde, followed by drying. A composited amount of GAC was 0.3 mg/cm.

The inner surface of the tube was observed by a scanning electron microscope. The composited GAC formed films between the fibrils of EPTFE partially, and unevenness of 0.5 to 1 µm was formed on the surface. Some parts of the inner wall were not covered by GAC. When this composite artificial blood vessel was flexed at a radius of curvature of 5 mm repeatedly, GAC was easily peeled off.

Each of six treated tubes was inplanted in a carotid artery of a rabbit. After four weeks, a patency ratio decreased to 17%.

FIG. 1 is a scanning electron microphotograph of an inner surface of the artificial blood vessel of Example 1 comprising EPTFE to which gelatinated atelocollagen is chemically bonded.

Figure 2:
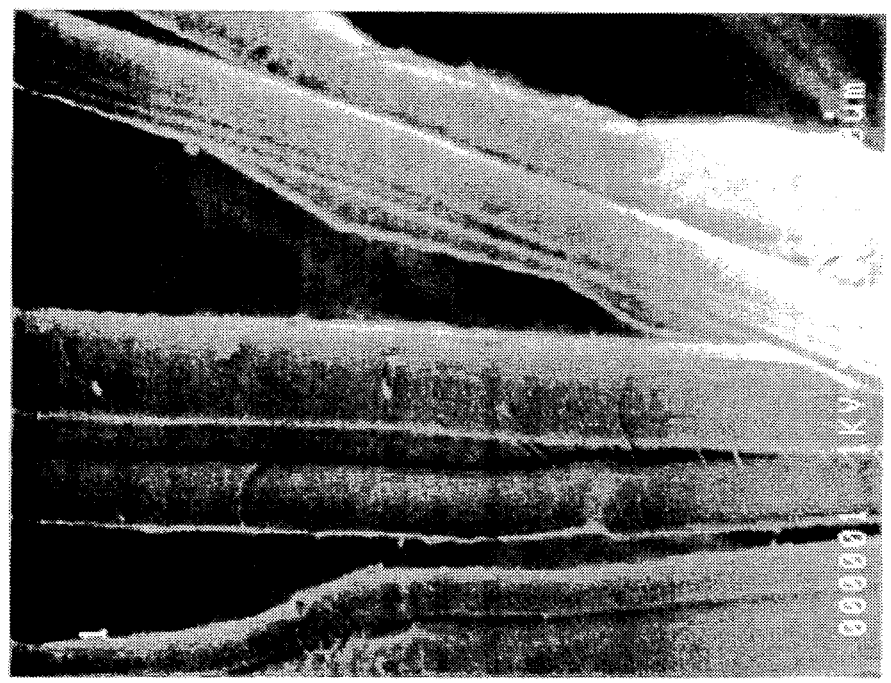
FIG. 2 is a scanning electron microphotograph of an inner surface of the conventional artificial blood vessel of Comparative Example 2 comprising EPTFE to which gelatinated atelocollagen is coated and crosslinked using glutaraldehyde.

FIG. 2 is a scanning electron microphotograph of an inner surface of the artificial blood vessel of Comparative Example 2 comprising EPTFE to which gelatinated atelocollagen is coated and crosslinked using glutaraldehyde.

Figure 3:
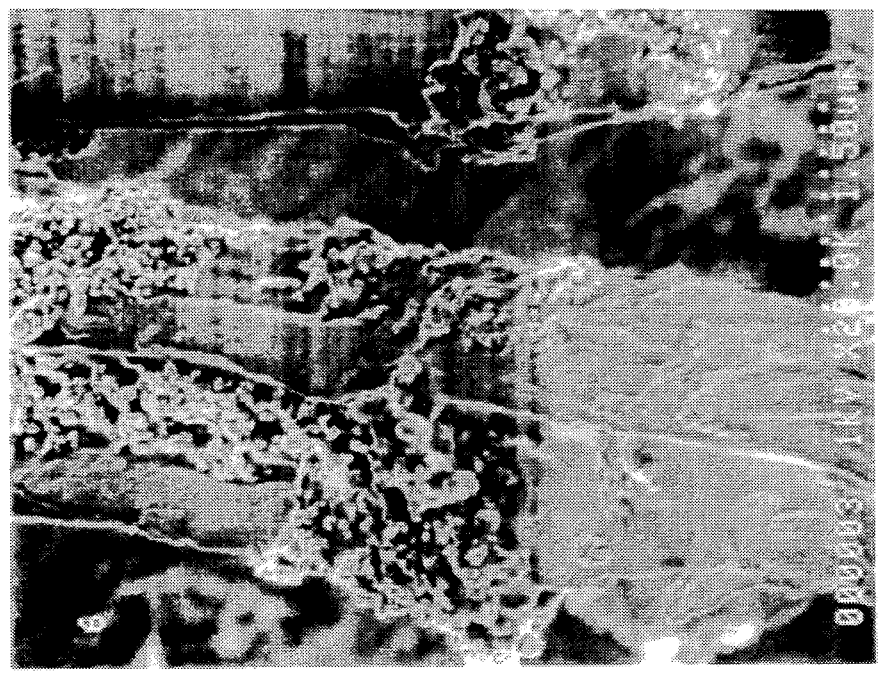
FIG. 3 is a scanning electron microphotograph of an inner surface of the untreated EPTFE artificial blood vessel of Comparative Example 1.

FIG. 3 is a scanning electron microphotograph of an inner surface of the untreated EPTFE artificial blood vessel of Comparative Example 1.

In the artificial blood vessel of the present invention, the gelatinated atelocollagen was thinly and uniformly composited and the shape of EPTFE was completely maintained, while the conventional one had the unevenness of several μm.

EFFECTS OF THE INVENTION

As explained above, the surface of the composite artificial blood vessel of the present invention is uniformly composited stably with the material having the tissue induction function by the covalent bond without deforming the shape of the porous synthetic polymer material. Therefore, by the synergistic effect with the porous structure, in particular, the porous structure of EPTFE, initial thrombus is hardly induced, and the intima is quickly formed and remains stably for a long time.

Accordingly, the composite artificial blood vessel of the present invention is useful as a substitute blood vessel of a small diameter blood vessel such as coronary artery, peripheral artery and the like with which no conventional material can achieve good patency.

What is claimed is:

1. An artificial blood vessel comprising:

a tube formed from expanded polytetrafluoroethylene having a porosity of at least 70% and a pore diameter from 20 to 200 μm, said tube having an inner and an outer surface on which is grafted a compound having a functional group selected from the group consisting of hydroxyl, carboxyl, epoxy and amino, wherein said functional group has been introduced onto said tube by defluorinating said polytetrafluoroethylene with an alkali metal compound and grafting thereto a compound having said functional group; and a material having cell adhesion and growth functions selected from the group consisting of proteins and peptides, covalently bonded through said functional groups to said inner and outer surfaces of said tube such that voids associated with the expanded polytetrafluoroethylene remain unclogged, and said material is present on said tube as a uniform, flexible and thin layer.

2. The artificial blood vessel according to claim 1, wherein said material having the cell adhesion function is at least one protein selected from the group consisting of collagen, gelatin, laminin and fibronectin.

3. The artificial blood vessel according to claim 1, wherein said material is gelatinized atelocollagen.

4. The artificial blood vessel according to claim 1, wherein said alkali metal compound to be used for defluorination is selected from the group comprising methyllithium, n-butyllithium or tert.-butyl-lithium, and is used in combination with hexamethylphosphoric triamide for the defluorination of polytetrafluoroethylene.

5. The artificial blood vessel according to claim 1 wherein the thin layer is characterized by an unevenness of less than 50 nm.

* * * * *

UNITED STATES PATENT AND TRADEMARK OFFICE
CERTIFICATE OF CORRECTION

PATENT NO.   : 5,591,225
DATED        : January 7, 1997
INVENTOR(S)  : OKUDA

It is certified that error appears in the above-identified patent and that said Letters Patent is hereby corrected as shown below:

On the title page, Item

Please change:

"[73] Assignee: Vascular Craft Research Center Co., Ltd. Tokyo, Japan"

to

--[73] Assignee: Vascular Graft Research Center Co., Ltd. Tokyo, Japan--

Signed and Sealed this

Seventeenth Day of June, 1997

Attest:

BRUCE LEHMAN

*Attesting Officer*    *Commissioner of Patents and Trademarks*